(12) United States Patent
Gervais et al.

(10) Patent No.: US 7,160,109 B2
(45) Date of Patent: Jan. 9, 2007

(54) TORQUE LIMITING IMPLANT DRIVE SYSTEM

(75) Inventors: Christopher Gervais, San Marcos, CA (US); Jeffery Bassett, Vista, CA (US); Carl Pettersen, San Diego, CA (US)

(73) Assignee: Sulzer Dental Inc., Carlsbad, CA (US)

( * ) Notice: Subject to any disclaimer, the term of this patent is extended or adjusted under 35 U.S.C. 154(b) by 45 days.

(21) Appl. No.: 10/183,211

(22) Filed: Jun. 27, 2002

(65) Prior Publication Data

US 2003/0054318 A1   Mar. 20, 2003

Related U.S. Application Data

(60) Provisional application No. 60/322,620, filed on Sep. 17, 2001.

(51) Int. Cl.
*A61C 3/00* (2006.01)

(52) U.S. Cl. .................................................. 433/141

(58) Field of Classification Search ............... 433/141, 433/173, 174, 175; 81/471, 467
See application file for complete search history.

(56) References Cited

U.S. PATENT DOCUMENTS

| | | |
|---|---|---|
| 2,112,007 A | 3/1938 | Adams |
| 3,067,740 A | 12/1962 | Haboush |
| 3,488,779 A | 1/1970 | Christensen |
| 3,846,846 A | 11/1974 | Fischer |
| 4,027,392 A | 6/1977 | Sawyer et al. |
| 4,234,309 A | 11/1980 | Sellers |
| 4,463,753 A | 8/1984 | Gustilo |
| 4,468,200 A | 8/1984 | Munch |
| 4,480,997 A | 11/1984 | Deutsch et al. |
| 4,484,570 A | 11/1984 | Sutter et al. |
| 4,553,942 A | 11/1985 | Sutter |
| 4,655,711 A | 4/1987 | Weissman |
| 4,668,191 A | 5/1987 | Plischka |
| 4,713,003 A | 12/1987 | Symington et al. |
| 4,713,004 A | 12/1987 | Linkow et al. |
| 4,722,688 A | 2/1988 | Lonca |
| 4,738,623 A | 4/1988 | Driskell |
| 4,758,161 A | 7/1988 | Niznick |
| 4,790,753 A | 12/1988 | Fradera |
| 4,793,808 A | 12/1988 | Kirsch |
| 4,802,848 A | 2/1989 | Randin |
| 4,826,434 A | 5/1989 | Krueger |
| 4,851,008 A | 7/1989 | Johnson |
| 4,854,872 A | 8/1989 | Detsch |
| 4,856,994 A | 8/1989 | Lazzara et al. |
| 4,863,383 A | 9/1989 | Grafelmann |
| 4,915,628 A | 4/1990 | Linkow et al. |
| 4,915,629 A | 4/1990 | Sellers |
| 4,927,363 A | 5/1990 | Schneider |
| 4,932,868 A | 6/1990 | Linkow et al. |

(Continued)

*Primary Examiner*—Melba Bumgarner
(74) *Attorney, Agent, or Firm*—Fitch, Even, Tabin & Flannery

(57) ABSTRACT

The disclosed drive system and fixture mount self limit the torque that can be applied to an implant during implantation to a value that is nondamaging to the implant. System components include releasably engaging elements. In certain embodiments, elements deform, elastically or permanently, to limit the applied torque. The fixture mount serves as an impression post and abutment for a temporary prosthesis and is subject to chair side modifications by the surgeon. Methods of shaping the fixture mount for use as an abutment and making a dental restoration using the shaped abutment are disclosed.

23 Claims, 6 Drawing Sheets

U.S. PATENT DOCUMENTS

| | | |
|---|---|---|
| 4,934,935 A | 6/1990 | Edwards |
| 4,955,811 A | 9/1990 | Lazzara et al. |
| 4,960,381 A | 10/1990 | Niznick ................ 433/174 |
| 4,976,617 A | 12/1990 | Carchidi |
| 4,988,297 A | 1/1991 | Lazzara et al. |
| 4,988,299 A | 1/1991 | Branemark |
| 4,995,810 A | 2/1991 | Soderberg |
| 5,015,186 A | 5/1991 | Detsch |
| 5,018,970 A | 5/1991 | Stordahl |
| 5,026,280 A | 6/1991 | Durr et al. |
| 5,026,285 A | 6/1991 | Durr et al. |
| 5,030,095 A | 7/1991 | Niznick |
| 5,030,096 A | 7/1991 | Hurson et al. |
| 5,035,619 A | 7/1991 | Daftary |
| 5,049,073 A | 9/1991 | Lauks |
| 5,061,181 A | 10/1991 | Niznick |
| 5,062,800 A | 11/1991 | Niznick |
| 5,064,425 A | 11/1991 | Branemark et al. |
| 5,073,111 A | 12/1991 | Daftary |
| 5,076,788 A | 12/1991 | Niznick |
| 5,078,607 A | 1/1992 | Niznick |
| 5,100,323 A | 3/1992 | Friedman et al. |
| 5,106,300 A | 4/1992 | Voitik |
| 5,108,288 A | 4/1992 | Perry |
| 5,125,840 A | 6/1992 | Durr et al. |
| 5,145,372 A | 9/1992 | Daftary et al. |
| 5,167,664 A | 12/1992 | Hodorek |
| 5,176,050 A * | 1/1993 | Sauer et al. ................ 81/471 |
| 5,180,303 A | 1/1993 | Hornburg et al. |
| 5,188,800 A | 2/1993 | Green, Jr. et al. |
| 5,197,881 A | 3/1993 | Chalifoux |
| 5,205,745 A | 4/1993 | Kamiya et al. |
| 5,209,659 A | 5/1993 | Friedman et al. |
| 5,254,005 A | 10/1993 | Zuest |
| 5,269,685 A | 12/1993 | Jorneus et al. |
| 5,281,140 A | 1/1994 | Niznick |
| 5,282,746 A | 2/1994 | Sellers et al. |
| 5,297,963 A | 3/1994 | Dafatry |
| 5,312,254 A | 5/1994 | Rosenlicht ................ 433/173 |
| 5,312,256 A | 5/1994 | Scortecci |
| 5,316,476 A | 5/1994 | Krauser |
| 5,324,199 A | 6/1994 | Branemark |
| 5,336,090 A | 8/1994 | Wilson, Jr. et al. |
| 5,338,196 A | 8/1994 | Beaty et al. |
| 5,362,235 A | 11/1994 | Daftary |
| 5,364,268 A | 11/1994 | Lazzara et al. |
| 5,366,374 A | 11/1994 | Vlassis |
| 5,368,160 A | 11/1994 | Leuschen et al. |
| 5,413,480 A | 5/1995 | Musikant et al. |
| 5,415,545 A | 5/1995 | Shaw |
| 5,431,567 A | 7/1995 | Daftary |
| 5,433,665 A * | 7/1995 | Beaty et al. ................ 464/38 |
| 5,435,723 A | 7/1995 | OBrien |
| 5,437,550 A * | 8/1995 | Beaty et al. ................ 433/141 |
| 5,437,551 A | 8/1995 | Chalifoux |
| 5,449,291 A | 9/1995 | Lueschen et al. ........... 433/173 |
| 5,468,150 A | 11/1995 | Brammann |
| 5,482,463 A | 1/1996 | Wilson, Jr. et al. |
| 5,484,285 A | 1/1996 | Morgan et al. |
| 5,538,428 A | 7/1996 | Staubli |
| 5,580,246 A | 12/1996 | Fried et al. |
| 5,591,029 A | 1/1997 | Zuest |
| 5,622,500 A | 4/1997 | Niznick |
| 5,630,717 A | 5/1997 | Zuest et al. |
| 5,695,336 A | 12/1997 | Lazzara et al. |
| 5,702,346 A | 12/1997 | Lazzara et al. |
| 5,704,788 A | 1/1998 | Milne |
| 5,709,547 A | 1/1998 | Lazzara et al. |
| 5,733,123 A | 3/1998 | Blacklock et al. |
| 5,755,575 A | 5/1998 | Biggs |
| 5,897,319 A | 4/1999 | Wagner et al. |
| 5,927,979 A | 7/1999 | Misch et al. |
| 6,068,480 A | 5/2000 | Misch et al. |
| 6,083,004 A | 7/2000 | Misch et al. ................ 433/173 |
| 6,086,371 A | 7/2000 | Bassett et al. ............... 433/173 |
| 6,247,933 B1 | 6/2001 | Wagner et al. |

\* cited by examiner

TORQUE LIMITING IMPLANT DRIVE SYSTEM

CROSS-REFERENCE TO RELATED APPLICATIONS

This application claims benefit of priority of U.S. Provisional Application Ser. No. 60/322,620, filed Sep. 17, 2001.

BACKGROUND OF THE INVENTION

1. Field of the Invention

The present invention relates generally to the field of dental implantogy and, more specifically, to apparatus for safely and effectively installing the implant in a prepared surgical site without damaging the implant.

2. Background Information

Dental implants play an extraordinarily important role in modem dentistry. Implants serve as the foundation for a variety of dental prostheses as may be provided to correct debilitating or embarrassing conditions caused by, for example, disease, accident or natural aging.

In order to adequately support the dental prosthesis for which it is intended, the implant (also referred to as a "fixture") is surgically implanted into healthy bone tissue of the patient's alveolar (jaw) bone. To install the implant, the surgical site is prepared by first incising the gingival tissue at the implant site and then drilling a generally cylindrical bore into the bone mass. The prepared bore is referred as an osteotomy. Although implants may be made in a variety of forms, a conventional and a very common implant has a generally cylindrical body that is externally threaded and tapered at one end. The taper may extend for only the distance of the first few threads or extend for nearly the entire length of the implant. In recent years, it has become conventional to apply certain coatings to the outer surfaces of the implants. These coatings, such as hydroxyapatite (HA) or Titanium Plasma Spray (TPS), enable the bone tissue to better integrate with the implant, thereby providing enhanced support for the prosthesis.

Once the osteotomy is prepared, the tapered end of the implant is positioned in the osteotomy, and a powered or manual driving tool is employed by the surgeon to rotate the implant and drive it into the osteotomy, which may or may not have been pre-threaded or tapped to receive the implant. The driving tool includes an end portion that is configured to matingly engage the end of the implant so as to transmit torque to the implant.

In some instances, both to deliver the implant to the surgical site and to drive the implant into the osteotomy, a piece referred to as a "fixture mount" is attached to the top of the implant by a retaining screw and it, rather than the implant, directly engages the driving tool. In this manner, the fixture mount serves as an intermediate member for transmitting to the implant the torque applied by the driving tool. Conventional fixture mounts have been made of metal, such as titanium.

The size of the osteotomy and the density of the bone mass at the surgical site will dictate the amount of torque that must be applied to the implant during installation. For example, where the bone density is greater than anticipated, the dental surgeon may find that an unusually high torque is required in order to implant the device. Presently, if the surgeon believes, based on tactile feedback, that the implant is experiencing excessive resistive force, such that a potentially damaging torque would have to be applied in order to install the implant, the surgeon must extract the then partially-installed implant. Typically, this is accomplished by reversing the drive tool's direction of rotation, and using the drive tool and fixture mount to "back-out" the implant from the osteotomy, which can then be widened with a larger drill or tapped as necessary.

If this procedure is not followed and, instead, an excessive torque is applied to the implant, the implant may become damaged. Such damage may take various forms. For example, the coating that is applied to the surface of the implant and that is important for enhancing bone growth may be scrapped off the implant or otherwise damaged. Furthermore, with increasing torque, the end of the implant that receives the applied torque may become damaged, much the way the head of a screw or bolt becomes stripped or rounded off. Finally, it is possible that the implant would fracture with excessive torque applied. In each instance, such damage typically would necessitate removal of the damaged implant, thereby lengthening the time required for the surgical procedure and, potentially, increasing the discomfort to the patient.

Further, with excessive torque applied to the top or driven end of the implant via the drive tool and fixture mount, the damage to the end of the implant may be such that it becomes impossible to simply back the implant out of the osteotomy using the drive tool and the fixture mount. This can further complicate the surgical procedure. Given that the implant cannot simply be backed out by rotating it in the opposite direction via the drive tool and fixture mount, other special tools and procedures need to be employed.

Once the implant is successfully installed, the still-attached fixture mount is in position to serve other functions. For example, by extending above the gum line as it does, the fixture mount may be employed to shape or direct the growth of gingival tissue during healing. Likewise, the fixture mount may be used as an impression post so that the dental surgeon or clinician may take precise impressions that are then used by a dental laboratory to manufacture a properly fitting prosthesis. Furthermore, the attached fixture mount may serve as a temporary abutment for supporting a provisional or temporary prosthesis that may be installed at the time of the original surgery and remain in place until the permanent prosthesis has been manufactured in a dental laboratory.

For use in any of these applications, however, the fixture mount may require certain modifications, particularly when used to support a temporary prosthesis. Such modifications may involve, for example, cutting, grinding or otherwise shaping the body of the fixture mount. Given that fixture mounts have been made typically of titanium or similar such metals, it has been common practice for the dental surgeon to purchase a separate component for use as the temporary abutment, one that is easier to prepare "chair-side" or that can be sent to a dental laboratory for the custom shaping that is necessary. In such instances, the fixture mount itself is discarded and the patient may be deprived of the opportunity of having a temporary prosthesis fitted at the end of the initial surgical procedure and must instead suffer the inconvenience of returning for a second procedure at a time when the temporary abutment and prosthesis can be installed. Still a third procedure is then required after the permanent prosthesis has been fabricated and is ready for installation.

Although it would be desirable for the dental surgeon himself to modify the fixture mount "chair-side," rather than sending the piece offsite to be altered or reconfigured for use as a temporary abutment, for example, the tools available to the dental surgeon typically limit his ability to shape the fixture mount. As mentioned above, conventional fixture mounts are typically made of titanium or another very strong metal. That factor, coupled with the very small size of the fixture mount, makes it extremely difficult for the dental surgeon to make precise chair-side modifications to the fixture mount.

Accordingly, given the damage that can occur to an implant if excessive torque is applied during implantation, it would therefore be advantageous to employ an implant drive system that would limit the torque or rotational force that can be applied to the implant. Preferably, the system would incorporate and could be employed with the driving tools and implants that are presently on the market and in the current inventories of dental surgeons. Preferably, the system would limit the rotational force or torque applied to the implant to a value below that which could damage the implant and, at the same time, provide a means to withdraw the implant from the osteotomy using the same system components, rather than by having to employ additional tools or a cumbersome or more complicated procedure. Further, it would be advantageous if a drive system included a fixture mount that could be readily revised or fashioned chair-side by the dental surgeon, such that a temporary or provisional prosthesis could be fitted and installed during the same surgical procedure in which the implant is first installed.

BRIEF SUMMARY OF PREFERRED EMBODIMENTS OF THE INVENTION

There is provided herein an apparatus and system for installing an implant into a prepared surgical site and limiting the applied torque to prevent the implant from being damaged. The system generally includes an implant, a drive tool for supplying rotational force to the implant, and a fixture mount that is disposed between and aligned with the implant and the drive tool, and that transmits the rotational force applied by the drive tool to the implant. Also disclosed is a method for installing the implant with the fixture mount and, thereafter, employing the fixture mount as an impression post and abutment for a temporary prosthesis.

According to a preferred embodiment of the invention, at least one end of the fixture mount includes an end portion that releasably engages the adjacent end of either the drive tool or the implant, as the case may be, and that is adapted to receive the applied torque and transmit it to the implant so long as the torque does not exceed a predetermined value. At torque exceeding that value, the end portion disengages itself from the adjacent member and ceases to transmit torque to the implant.

In certain embodiments, the end portion includes a deformable socket or a deformable extending member that, in each instance, mates with a correspondingly sized and configured structure of the drive tool or implant. The socket may include a single recess having a non-circular shape, such as a hexagon or other polygon, or it may include an array of recesses, such as an array of slots, or holes. Likewise, the extending member may be a single extension having a non-circular cross section, or may be an array formed by a plurality of extensions. When the predetermined torque is exceeded, either elastic or permanent deformation of the part occurs. In the case of elastic deformation, the socket or extension returns to its original configuration once the drive tool is axially displaced from the fixture mount. By then re-engaging the tool with the fixture mount and reversing the direction of the drive tool, the fixture mount is employed to remove the implant so that the osteotomy can be further prepared. In the instance of permanent deformation, the invention permits the dental surgeon to sever the now-deformed end of the fixture mount and employ the remaining, non-deformed portion to remove and then reinstall the implant. According to the invention, the part undergoing deformation can be either end of the fixture mount (or both ends) or can be the end of the drive tool.

Some embodiments of the invention also include a structure and means to provide a back-up or secondary torque limitation. In a preferred embodiment, the end of the fixture mount adjacent to the drive tool first disengages and limits the torque to the first predetermined value. As a backup torque limiting mechanism, the end of the fixture mount adjacent the implant is adapted to disengage at a second predetermined torque that is greater than the first torque, but one that is still less than that which could damage the implant. Similarly, the primary torque limitation can occur at the interconnection between the fixture mount and the implant, with the secondary limitation being provided at the interconnection between the fixture mount and the drive tool. In either instance, this embodiment of the invention can thus provide a hierarchy of torque limiting structures.

The interconnection or interface between the fixture mount and the other system components may provide torque limitation also by means of matingly engaging sockets and extensions having engaging surfaces that resist relative movement until a predetermined torque is exceeded, at which time the frictional forces between the engaging surfaces are overcome such that rotation of one member no longer causes rotation of the matingly engaged member. When the limiting torque is reached, the parts rotate relative to one another such that torque is no longer transmitted. In certain embodiments, these structures may include an extending member having a frustoconical outer surface matingly received within a socket having a similarly sized and shaped frustoconical recess. Likewise, the extension and mating recess may be cylindrical in shape.

To provide certain of the advantages of the invention, it is preferred that the material from which the fixture mount is fabricated be a plastic, such as a thermoset plastic or a thermoplastic. These materials, in addition to facilitating the torque limitation desired of the present invention, also yield a fixture mount that may readily serve as an abutment for a temporary prosthesis, one that is easy to shape or modify by a dental surgeon during the same procedure in which the implant is installed. The fixture mount and abutment thus contemplated by this embodiment of the invention may include longitudinal channels and circumferential grooves on the outer surface to prevent rotation of the temporary prosthesis. Further the channels and grooves ensure retention of the fixture mount/abutment in the impression materials that are typically used to transfer the position and orientation of the implant in the mouth to a dental stone model. In this manner, the fixture mount is therefore also particularly suited for use as an impression post employed to facilitate the construction of a properly fitting and aesthetically pleasing permanent prosthesis.

More specifically, the state of the art in implant dentistry is to place the implant, take an impression immediately after placement, and then to provide the patient with a temporary abutment and temporary prosthesis all in the same session. This procedure minimizes the time required to complete the implant restoration because fabrication of the final or permanent prosthesis can begin based on the impression taken at the time of surgery, and because both hard and soft tissue healing can begin with the temporary abutment in place. Further, the patient leaves the surgery with an aesthetically pleasing, and in many cases, functional restoration and may not be required to return to the dental office until the final prosthesis has been fabricated. The plastic fixture mount of certain preferred embodiments is thus particularly suited to perform multiple functions: to limit torque applied to the implant during installation; to provide an impression post that supplies implant location and orientation to the dental laboratory; and to provide an abutment to support a temporary prosthesis.

Accordingly, the present invention comprises a combination of features and advantages, which enable it to overcome various problems, deficiencies or shortcomings associated with prior devices. The various characteristics described above, as well as other features of the invention, will be readily apparent to those skilled in the art upon reading the following detailed description of the preferred embodiments of the invention, and by referring to the accompanying drawings.

BRIEF DESCRIPTION OF THE DRAWINGS

For a more detailed description of preferred embodiments of the present invention, reference will now be made to the accompanying drawings, wherein.

DETAILED DESCRIPTION OF PREFERRED EMBODIMENTS

Figure 1:
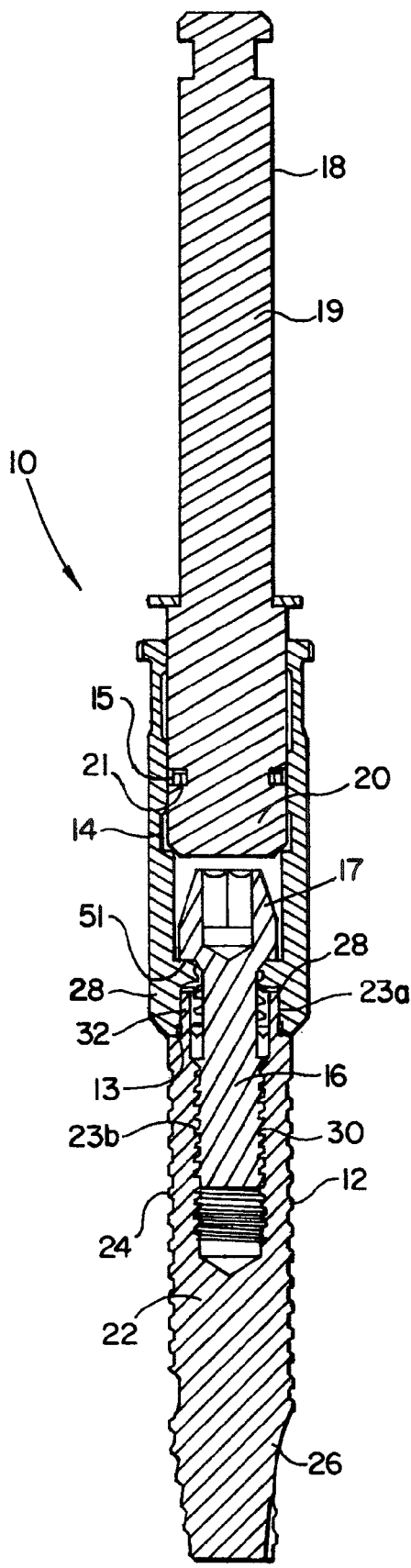
FIG. 1 is a cross sectional view of an implant drive system made in accordance with a preferred embodiment of the present invention.

A torque limiting implant drive system 10 employing the features of the present invention is shown in FIG. 1. System 10 includes dental implant 12, fixture mount 14, retaining screw 16 and drive tool 18, all coaxially aligned in use. Drive system 10 may be employed to install any one of a variety of implants.

Implant 12 is preferably made of titanium or another strong and biocompatible metal and includes a generally cylindrical body 22 having external threads 24, tapered end 26 and coronal end 28 for mateingly engaging with fixture mount 14. Implant 12 further includes a central threaded bore 30 for engaging corresponding threads of retaining screw 16. Coronal end 28 of implant 12 includes upwardly extending projections or splines 32 that are received within and engaged by corresponding structure formed on fixture mount 14, as described below in more detail. An implant 12 having splines 32 is described in more detail in U.S. Pat. No. 5,449,291, the entire disclosure of which is hereby incorporated by reference. Retaining screw 16 includes head 17 and upper and lower threads 23a, 23b, respectively.

Referring still to FIG. 1, drive tool 18 includes shaft 19 and hex-shaped extending portion 20. As understood in the art, shaft 19 mates with a hand tool (not shown) that, upon actuation by the dental surgeon, rotates shaft 19 and extension 20 in a preselected direction and at a predetermined speed. Hex-shaped extension 20 provides a mating interface with fixture mount 14 as described in more detail below, and may include a ring or clip 15 disposed in groove 21 to provide increased frictional force for retaining fixture mount 14 on drive extension 20.

Referring now to FIGS. 2–6, fixture mount 14 includes a generally elongate body 34 having axis 11, an outer surface 35, an implant engaging end 36, a drive tool engaging end 38, a central cavity 40, and flange 46 adjacent drive tool engaging end 38. The outer surface 35 of body 34 includes flats 42 formed longitudinally on the body, and a groove 44 formed about body 34 generally adjacent to flange 46. Groove 44 provides a means for engaging a removable collar such as shown and described in U.S. Pat. No. 6,086,371, the entire disclosure of which is incorporated herein by reference. Such a collar may be employed to suspend fixture mount 14 and implant 12 within a sterile delivery container. As best understood with reference to FIGS. 5 and 6, flats 42 are positioned circumferentially about body 34 at locations less than 180 degrees apart (their surfaces being formed at an angle $\alpha$ relative to one another) so as to provide body 34 with an orienting extension or lobe 43 as is useful when fixture mount 14 serves as an impression post or temporary abutment. In the embodiment shown, $\alpha$ is preferably approximately 60°. The orienting lobe 43 and flats 42 (which alternatively may be channels) ensure that a prosthesis made from impressions taken of fixture mount 14 after the implant 12 is installed will resist rotation, will be properly oriented, and will correctly match the position of the implant. To ensure a properly-fitting prosthesis, flange 46 provides a surface that is perpendicular with respect to axis 11 for acting against the impression material when fixture mount 14 serves as an impression post, and against the acrylic or other material used in fabricating a temporary prosthesis when the fixture mount serves as a temporary abutment.

Figure 4:
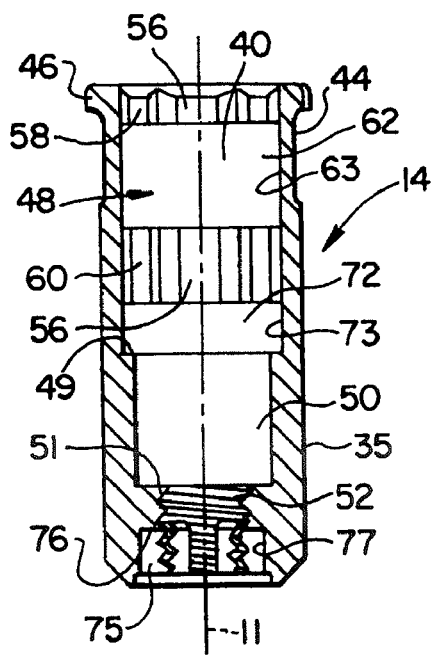
FIG. 4 is a cross sectional view of the fixture mount shown in FIG. 3 as taken along line 4—4.
Figure 3:
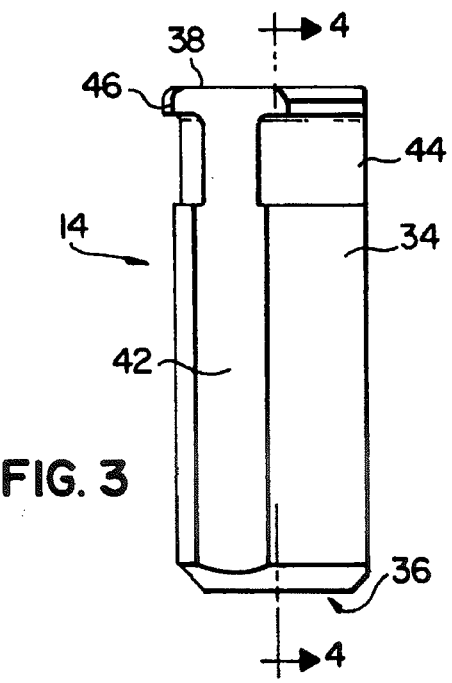
FIG. 3 is an elevation view of the fixture mount shown in FIG. 2.
Figure 6:
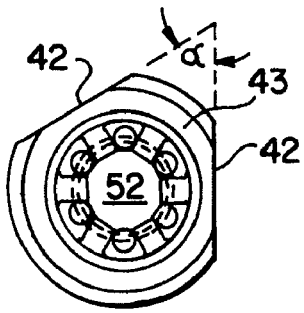
FIG. 6 is an end view of the bottom or implant-engaging end of the fixture mount shown in FIG. 3.

As best shown in FIG. 4, central cavity 40 of fixture mount 14 includes a socket 48 for mating and releasably engaging extension 20 of drive tool 18 (FIG. 1), a central bore 50, and a threaded bore 52. Socket 48 is co-axially aligned with and interconnects to central bore 50 at shoulder 49. Bore 50 extends between socket 48 and threaded bore 52, bore 50 interconnecting threaded bore 52 at shoulder 51. Bore 50 is formed to have a diameter large enough to accommodate head 17 of retaining screw 16 (FIG. 1). Threaded bore 52 extends between implant engaging end 36 and central bore 50 and is coaxially aligned with bore 50.

In fixture mount 14 shown in FIGS. 1–6, socket 48 includes banded segments 58, 60 each having a hex-shaped opening defined by flats 56. Bands 58, 60 are separated by an annular recess 62 having a generally cylindrical surface 63. A similar annular recess 72 with cylindrical surface 73 is formed between band 60 shoulder 49, with recesses 62, 72 having substantially the same diameter and a diameter that is greater than the diameter of bore 50. Flats 56 and bands 58, 60 are sized to engage corresponding flat surfaces on the hexagonal extension 20 of drive tool 18, socket 48 and drive tool extension 20 providing an interconnection or joint through which torque is transferred from the drive tool to the fixture mount.

Figure 2:
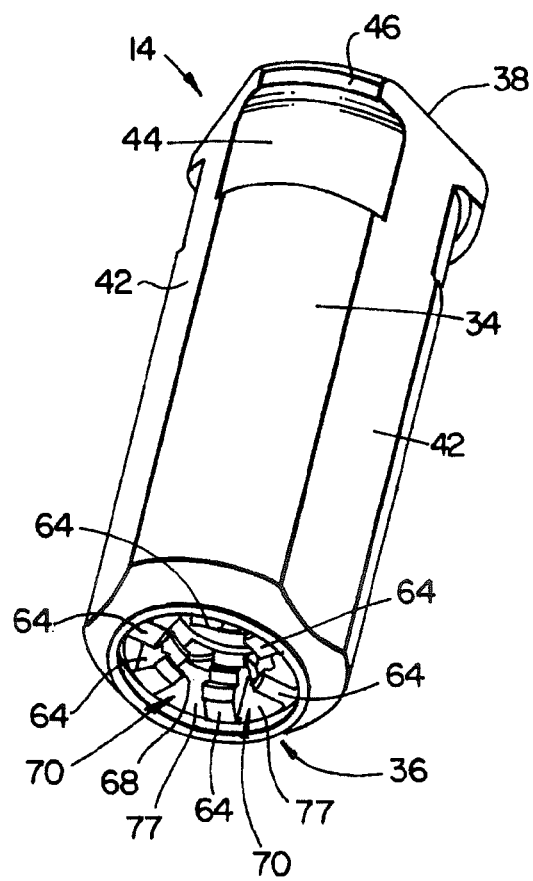
FIG. 2 is a perspective view of the fixture mount of the drive system shown in FIG. 1.
Figure 5:
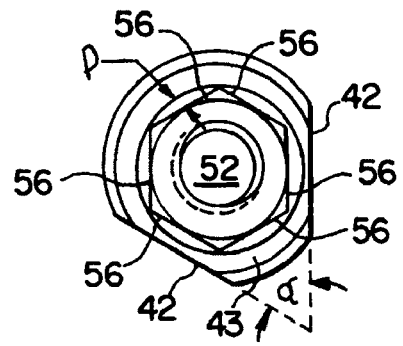
FIG. 5 is an end view of the top or coronal end of the fixture mount shown in FIG. 3.

As best shown in FIGS. 2 and 4, implant engaging end 36 of fixture mount 14 includes an array of six splines 64 and a cylindrical recess or socket 75. Recess 75 includes a recess bottom 76 and a cylindrical side surface 77 and is co-axially aligned with threaded bore 52. Splines 64 are disposed approximately sixty degrees apart and extend axially from recess bottom 76 and radially from recess side surface 77. The radially innermost edges of splines 64 include threads 68 (best shown in FIG. 2). Threads 68 engage upper threads 23a of screw 16 (FIG. 1) such that, in an assembly step prior to shipment, screw 16 is captured within fixture mount 14 for the convenience of the dental clinician.

Referring again to FIGS. 2 and 6, the angularly spaced splines 64 create voids between the splines, such voids referred to herein as spline receptors 70, for receiving and inter-digitating with splines 32 that extend from implant 12, wherein each of the implant's splines 32 is disposed between a pair of splines 64 in a spline receptor 70. In this manner, recess 75 of the fixture mount and coronal end 28 of the implant form an interconnection or joint through which torque is transferred from the fixture mount to the implant.

Fixture mount 14 is preferably made of a plastic and, more particularly of a thermoset plastic or a thermoplastic. One such suitable material for fixture mount 14 is a polyetherimide (PEI) marketed by GE Plastics under the trade name Ultem®.

To provide torque limiting characteristics, it is desirable that the material from which the fixture mount is constructed be able to stretch a substantial degree before breaking. This characteristic is quantified by the elongation percentage of the material. Prior art fixture mounts were made of materials having relatively little ability to stretch. For example, titanium alloy 6A14V has an elongation percentage of 15. For comparison purposes, tungsten carbide has an elongation percentage of 0, high strength 4340 steel has an elongation percentage of 2.5, aluminum alloy 7075-T6 has an elongation percentage of 12. In this embodiment of the present invention, it is desirable that the fixture mount be made from a material having an elongation percentage of about 50 or above. Most preferably, the material should be selected so as to have an elongation percentage of greater than 60.

Generally, materials have two modes of deformation—elastic and plastic. The division between the two modes is referred to as the yield point of the material. Below the yield point, the material deforms elastically, meaning that the material will return to its original shape after the deforming load is removed. Above the yield point, the material deform plastically or permanently, meaning it will not return to its original shape and will remain at least partially deformed. Deformation in the elastic region is proportional to the elastic or Young's modulus of elasticity of a material.

Prior art fixture mounts of titanium do not have the desirable modulus of elasticity. For example, titanium 6A14V has a modulus of elasticity equal to about 100 GPa. Various other metals similarly have a high modulus of elasticity and thus lack the degree of flexibility desirable for the fixture mount preferred for the present invention. It is preferred that the material for the fixture mount of the present invention have a modulus of elasticity that is less than 45 GPa. It is more desirable that the material selected have a modulus of elasticity of less than 10 GPa and, still more preferably, less than 5 GPa. The Ultem® PEI referred to above as suitable for fixture mount 14 has an elongation percentage of 80 and a modulus of elasticity equal to 3.3 GPa.

Various thermoset plastics and thermoplastics are suitable for the present invention. In general terms, thermoplastics will return to their original configuration after being stretched. By contrast, a thermoset plastic provides the desired elasticity and elongation, but after stretching, it will not return entirely to its original unstretched configuration.

As understood by those skilled in the art, the precise configuration and dimensions of the various components of fixture mount 14 may vary depending upon the size of the implant to be installed and the characteristics of the material from which the fixture mount is fabricated. Thus, as an example only, one such fixture mount suitable for the present invention and made of Ultem®1000 is approximately 9.78 mm long and has an outer diameter of approximately 4.57 mm at flange 46 and an outer diameter of approximately 4.06 mm at implant engaging end 36. In this example, socket 48 has a depth of approximately 4.01 mm as measured from drive tool engaging end 38 to shoulder 49. Annular recesses 62, 72 have an overall diameter of approximately 3.28 mm. Banded segments 58, 60 are approximately 0.76 mm and 1.47 mm, respectively, in length and are separated by recess 62 that is approximately 2.03 mm in length, with recess 72 being approximately 1.01 mm in length. As represented by distance "D" shown in FIG. 5, flats 56 extend radially inward from recess 62 a distance that is approximately 0.66 mm measured at its most distant point. Given this configuration, socket 48 will deform and cease to transmit applied torque when a torque greater than approximately 63% of the ultimate torsion strength of the splined titanium implant is applied to the socket. As will be understood by those skilled in the art, in this configuration of socket 48, the predetermined torque at which the socket will cease to transmit applied torque may be varied by changing the widths of bands 58, 60 and the width of recess 62 (which defines the separation between bands 58, 60). By varying these features, as well as through the selection of the material used to fabricate the fixture mount, the torque at which socket 48 will deform may be precisely controlled.

The use of drive system 10 to install implant 12 is best described with reference to FIG. 1. As shown, the coronal end 28 of implant 12 is matingly received in the implant engaging end 36 of fixture mount 14 with the splines 32 of the implant being received in spline receptors 70. Retaining screw 16 secures fixture mount 14 to implant 12 by threadingly engaging threaded bore 52 and threads 68 on splines 64 of the fixture mount, and the internal threads in bore 30 of the implant. The screw head 17 bears against annular shoulder 51 within the fixture mount 14. Preferably, retaining screw 16, fixture mount 14 and implant 12 are pre-assembled prior to shipment to the dental surgeon, and are shipped within a sterile delivery container such as that disclosed in U.S. Pat. No. 6,086,371.

After preparation of the osteotomy, the hex extension 20 of drive tool 18 is fitted within socket 48 of fixture mount 14 and the assembly formed by fixture mount 14, implant 12 and retaining screw 16 is removed from its shipping container. Using the drive tool 18, the assembly is carried to the surgical site where the tapered end 26 of the implant is placed in the osteotomy. To install the implant, the surgeon will actuate the hand piece (or employ a manual drive) which in turn will rotate the drive tool 18. The hexagonal drive tool extension 20 engages flats 56 of socket 48 so that the rotational force from drive tool 18 is transmitted to fixture mount 14. In turn, the same force and torque is transmitted to implant 12 by means of the interdigitations of splines 64 of the fixture mount 14 and splines 32 of implant 12.

If the density of bone tissue at the surgical site matches expectations, the implant will be threaded into the osteotomy without experiencing potentially-damaging resistive forces. However, in the event that an excessive resistive force is encountered, the torque limiting features of the present invention will act to protect the implant from damage. Specifically, when the torque applied by drive tool 18 to fixture mount 14 increases to a pre-determined magnitude, hexagonal bands 58, 60 will undergo elastic deformation to such an extent that the hexagonal extension 20 of drive tool 18 rotates within fixture mount socket 48 and ceases to apply further rotation force to the fixture mount 14 or implant 12. Essentially, the hexagonal openings in bands 58, 60 stretch to such a degree that they can no longer transmit to the implant the rotational force. In such instance, the hexagonal extension 20 of the drive tool merely spines or rotates within socket 48 thereby signaling the dental surgeon that the torque required to completely thread the implant into the osteomony could potentially damage the implant. Accordingly, the surgeon will then remove the hexagonal extension 20 from the socket 48 and thereby allow the socket to return to its unstretched configuration. Thereafter, the extension is again inserted into the socket and, with the rotation drive tool now reversed, the implant can be backed out of the osteotomy allowing the site to be redrilled or tapped as necessary. When so prepared, the hex extension of the drive tool is again used to deliver the implant and fixture mount to the osteotomy and to install the implant at a torque below that which could damage the implant.

If desired, for example as a backup or secondary torque limiting mechanism, splines 64 in implant engaging end 36 of fixture mount 14 can be sized and configured to deform should the torque-limiting features at the drive tool engaging end 38 fail to limit torque as designed. In this manner, should socket 48 not deform to limit the torque applied to the implant below a first predetermined value, and should the torque being imparted to the implant then exceed a second pre-determined torque greater than the first, splines 64 will deform so as to protect the splines 32 on the coronal end of the implant from being damaged. As an example, with a splined implant such as implant 12 shown in FIG. 1 and having a diameter of 3.15 mm, socket 48 will deform at a torque of approximately 45% of the ultimate torsion strength of the implant so as to protect implant 12. In the same example, the splines 64 in the implant engaging end 36 of fixture mount 14 are configured to deform on a second pre-determined torque of approximately 66% of the ultimate torsion strength of the implant. Without regard to the precise torque selected as the first pre-determined torque limit, it is beneficial that the second limiting torque be between 30% and 100% greater than the first limiting torque, and preferably be between approximately 30%–50% percent greater than the first limiting torque.

Drive system 10 and fixture mount 14 described above thus provide significant advantage over the prior art where torque applied to the coronal end of the implant was not controlled or limited and where, therefore, the implant could be easily damaged and rendered unuseable. The fixture mount 14 has an additional advantage over prior titanium parts in that it can be injection molded, providing precise and economical manufacturing of the part.

In addition to offering a means for torque control, the non-metallic material preferred for the fixture mount 14 of FIGS. 1–6 has the additional advantage over titanium or other conventional metals when the surgeon or clinician desires to employ the fixture mount for use as a temporary abutment for a provisional or temporary prosthesis. As mentioned above, because the fixture mount is preassembled to the implant and extends above the gingival tissue, the fixture mount can conveniently serve as an impression post and as a temporary abutment to support a prosthesis. When used as an impression post, an impression of the fixture mount 14 and the attached implant is taken immediately after the implant is installed using a conventional elastomeric impression material. The impression replicates the flats, channels or grooves on the outer surface of the fixture mount so that, when an analog of the implant and fixture mount is cast at the dental laboratory using the impression, the position and orientation of the implant in the mouth is exactly duplicated.

For use in supporting a temporary prosthesis, it is many times desirable to shape or otherwise modify fixture mount 14 after the implant has been placed and the impression taken, and to do so chair side rather than having to send the piece to an offsite dental laboratory for revision. In the latter instance, the patient is inconvenienced by having to return to the clinician's office for a second visit, as well as by having to do without the temporary abutment and prosthesis in the interim. Softer materials, such as the thermoplastics or thermoset plastics preferred for the present invention, are easier to modify chair side than are the conventional metallic components. Thus, after fixture mount 14 is first employed to install implant 12 as previously described, screw 16 is then unthreaded from implant 12 so as to release fixture mount 14. The fixture mount is then removed from engagement with the implant and shaped or otherwise modified by the dental professional so that it is better suited to form the core or support for a temporary prosthesis. As used herein, the terms "shape" or "shaped" when used to describe the modifications made by the dental professional to the fixture mount to allow it to serve as an abutment for a prosthesis mean and include all processes which alter the size and/or shape of the fixture mount, including but not limited to cutting, severing, scrapping, grinding and the like.

Figure 19:
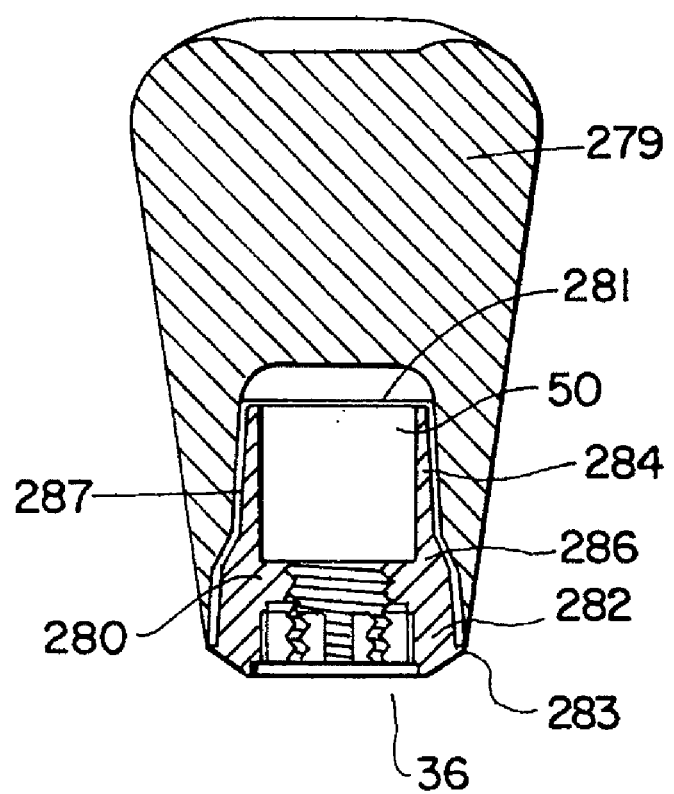
FIG. 19 is a cross sectional view of the fixture mount of FIG. 2 when employed as an abutment for a temporary, single tooth prosthesis.

Referring to FIG. 19, fixture mount 14 (previously described with reference to FIGS. 1–6) has been disengaged from the installed implant and then shaped by first severing drive tool engaging end 38 (FIG. 2) and approximately 50% of the length of the fixture mount so as to shorten the piece for use as an abutment 280.

In this example, fixture mount 14 is shown severed near shoulder 49 (FIG. 4) and above central bore 50 so as to form an abutment 280 having implant engaging end 36 and distal end 281. The outer surface of abutment 280 is then further shaped so as to conform to and better support temporary prosthesis 279. Preferably, abutment 280 is shaped to include a base segment 282, an end segment 284, and a shoulder 286 therebetween. Comparing abutment 280 in FIG. 19 to fixture mount 14 shown in FIG. 4, it can be seen that little material is removed from fixture mount 14 to form base segment 282. Thus, base segment 282 is only slightly tapered so as to provide a strong supporting base for prosthesis 279. Base segment 282 has its greatest diameter at flange 283 that engages and supports the terminus of prosthesis 279. End segment 284 preferably includes a frustoconical outer surface 287 that is tapered along its length to a greater degree than base segment 282. Depending on the particular application and the structure of the prosthesis to be supported, end segment 282 may instead include a substantially cylindrical outer surface. In either event, it is preferred that the portion of the base segment having the greatest diameter be larger in diameter than the diameter of the end segment 284 at any location along its length. Shoulder 286 forms a transition surface between base segment 282 and end segment 284 and preferably includes a frustoconical outer surface.

Once appropriately shaped to conform to the particular prosthesis being fitted, the modified fixture mount, now abutment 280, is reattached to installed implant 12 by retaining screw 16, and is then used to support the prosthesis 279 that is made or formed about abutment 280 using conventional methods. According to one such method, the tooth prosthesis 279 is formed directly on the abutment 280 using an acrylic material. The acrylic material bonds to the modified fixture mount because the plastic has an affinity for the plastic material that is preferred for the fixture mount 14, and because it is captured by the groove and slot geometry of the fixture mount. Alternatively, a preformed tooth prosthesis can be cemented to the abutment 280 and held in place by the same retentive geometry. This embodiment of the invention thus permits an implant to be installed, an impression taken, and a temporary prosthesis placed all in a single surgical setting. As used herein, the phrase "single surgical setting" when used to describe the timing associated with performing various procedures or steps means that all such steps are performed during a single visit to the office of the dental professional, as contrasted with performing those steps over multiple visits by the patient over various days or weeks.

Accordingly, fixture mount 14, when made of plastic, provides a single piece that is well suited as a fixture mount with torque limiting characteristics, an impression transfer mechanism, and an abutment for a temporary prosthesis. This makes it particularly suited for, but not limited to, use in the anterior of the mouth where implant diameter is limited by the narrow interdental spaces, and where the lack of a tooth for even a short time would be most noticeable.

Figure 7:
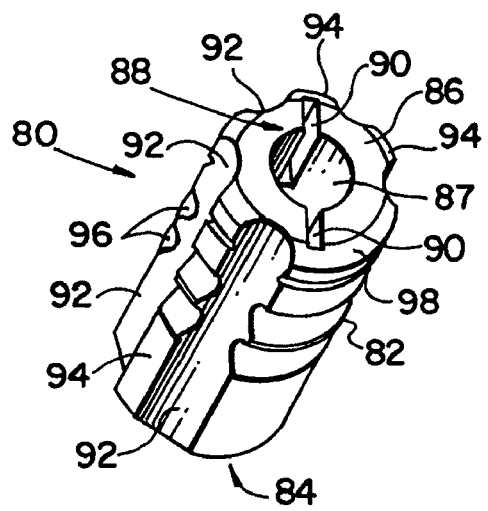
FIGS. 7–15 are each a perspective view of an alternative fixture mount of the present invention.

The system 10 of the present invention may employ fixture mounts configured in a number of ways to provide the desired torque limiting characteristics. One such alternative embodiment is shown in FIG. 7. As shown therein, fixture mount 80 comprises a generally cylindrical body 82 having implant engaging end 84, drive tool engaging end 86, central bore 87 and a tool-receiving socket 88 formed on tool engaging end 86. A retaining screw such as the one shown in FIG. 1 is disposed in bore 87 and interconnects fixture mount 80 with the implant as previously described. Socket 88 includes a pair of aligned and diametrically opposed slots 90. The outer surface of body 82 includes longitudinal channels 92 spaced circumferentially about the body so as to form a plurality of lobes 94 there between. One lobe 94 is larger than the others and forms an orienting lobe 98. Body 82 also includes circumferential grooves 96. As explained previously with respect to the embodiment of FIGS. 2–6, channels 92 and the orienting lobe 98 ensure that a prosthesis made from an impression of the fixture mount will be correctly positioned relative to the implant, and will not rotate after it has been installed. Grooves 96, like flange 46 in the embodiment of FIGS. 2–6, are useful in the impression process as they provide vertical surfaces (surfaces perpendicular to the axis of the fixture mount) for acting against the impression material. Implant engaging end 84 is configured so as to matingly engage the coronal end of the implant and, for a splined implant 12 such as shown in FIG. 1, for example, may be identical to implant engaging end 36 of fixture mount 14 previously described.

To install an implant using fixture mount 80, a drive tool is used that has either a single blade that is disposed within both slots 90 simultaneously, or a pair of blades, each one of which is installed in one slot 90. It is preferred that slots 90 have a depth measured in the axial direction equal to approximately twice the length of the extending drive tool blade, such that, once the drive tool blade is inserted to the maximum depth allowed by the tool, a substantial portion of slots 90 remain unfilled. As the drive tool is rotated, the torque is transmitted from the driving tool blade to the fixture mount and, in turn, to the implant. If the predetermined torque is exceeded, socket 88 is deformed by the drive tool blade to such an extent that the fixture mount ceases to transmit the torque. The deformation may be by the stretching of the material forming the socket, or by the tearing or shearing of socket material, or other phenomenon, although in this embodiment, it is preferred that the socket material be selected so as to permanently deform. When this occurs, the dental surgeon withdraws the drive tool blade and severs the deformed portion of the socket, leaving the lower portions of slots 90 intact and available for receiving the reinserted drive tool blade or blades. Then, after the osteotomy has been further prepared, the now-shortened fixture mount 80 can be used to install the implant as previously described.

Figure 8:
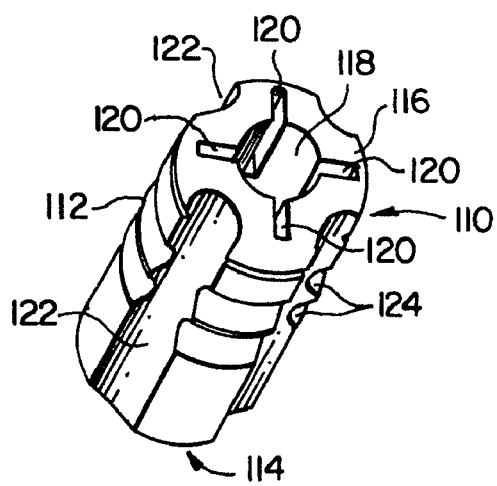

FIG. 8 shows another alternative fixture mount 110 that is similar to fixture mount 80 previously described. Fixture mount 110 includes body 112 having an implant engaging end 114 and drive tool engaging end 116. Body 112 includes longitudinal channels 122 and circumferential grooves 124 on its outer surface. Longitudinal channels 122 are spaced apart such that body 112 is generally cross-shaped in cross section. Although longitudinal channels 122 are shown angularly spaced approximately 90 degrees apart, the spacing of the grooves, and their numbers, may be varied so as to provide an orienting lobe. Tool engaging end 116 includes a socket 118 for receiving an extending segment of the drive tool. Socket 118 includes an array of four slots 120, with one slot formed in each extending lobe.

Socket 118 and slots 120 are sized and configured so as to receive correspondingly sized and shaped extensions of a drive tool. In this embodiment, the drive tool extension may be configured like the drive end of a phillips head screwdriver or may be formed by four extending tabs or splines. When the drive tool is completely inserted into socket 118, a substantial length of slots 120 remain unfilled and extend beneath the end of the drive tool extension. In this manner, when excessive torque is applied to socket 118 by the drive tool, the upper end of the socket 118 deforms so that further torque cannot be applied. As with fixture mount 80 previously described, the deformed end of implant 110 can then be severed by the surgeon and the drive tool reinserted to drive the implant using the undeformed and remaining sections of slots 120.

Figure 9:
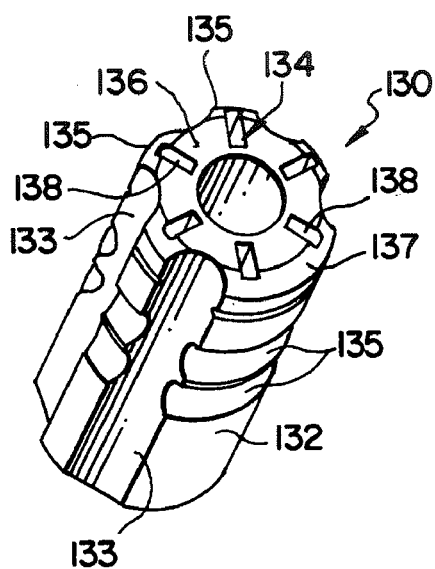

Another alternative embodiment of the invention is shown in FIG. 9, this embodiment being similar in many respects to the embodiment shown in FIG. 8. Referring to FIG. 9, fixture mount 130 includes body 132 having a drive tool engaging end 134 with socket 136. Socket 136 includes an array of six axially extending slots 138 that are sized and configured to matingly receive corresponding splines or tabs extending from a drive tool. As previously described, the axial depth of slots 138 exceeds the length of the drive tool splines and preferably are approximately two times as long as the drive tool's extensions. Body 132 includes longitudinal channels 133 spaced so as to form lobes 135, including and an orienting lobe 137.

Figure 10:
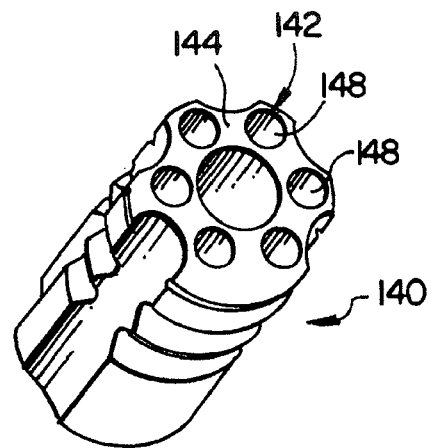

Another alternative embodiment of the fixture mount of present invention is shown in FIG. 10 wherein fixture mount 140 includes a socket 142 on drive tool engaging end 144. Socket 142 includes an array of six parallel bores 148 for receiving similarly configured cylindrical extensions of the drive tool. As previously described, the axial length or depth of bores 148 will be approximately twice the length of the cylindrical extensions so that, when a pre-determined maximum torque is applied to the fixture mount 140, the drive tool engaging end of the fixture mount will be deformed. However, by removing the deformed section of the fixture mount 140, the remaining length of the bores 148 may be used to install the implant using the fixture mount 140 and the drive tool.

Figure 11:
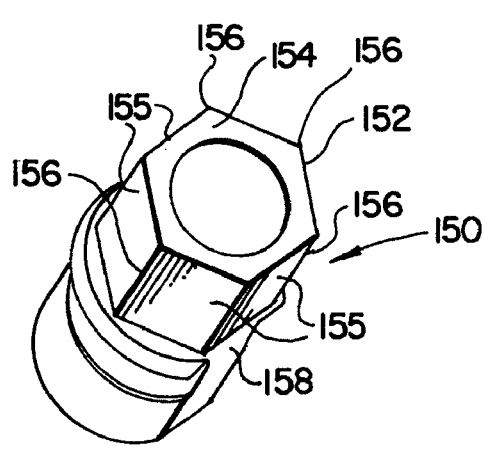

Heretofore, the drive tool engaging end of the fixture mount has been shown and described as having a socket comprising one or more polygonal openings, slots, or bores for receiving a correspondingly configured extension on the drive tool. Similarly, the fixture mount may be constructed such that the drive tool engaging end has one or more extensions that are sized and shaped so as to engage a correspondingly configured socket or receptacle in a drive tool. For example, referring to FIG. 11, a fixture mount 150 is shown having drive tool engaging end 152 including hexagonal extension 154. Hex extension 154 includes flats 155 intersecting at corners or edges 156. A drive tool to be employed with fixture mount 150 includes a hexagonal shaped socket sized to receive hex extension 154. Torque limiting with fixture mount 150 is controlled through the selection of appropriate material and the shape and size of the polygonal extension 154. In the embodiment shown in FIG. 11, when an excess torque is applied, the corners 156 of the polygonal extension will deform such that further rotation of the drive tool does not rotate the fixture mount or the attached implant. The fixture mount 150 includes one or more flats 158 formed about its length so as to provide for orientation and anti-rotation.

Figure 12:
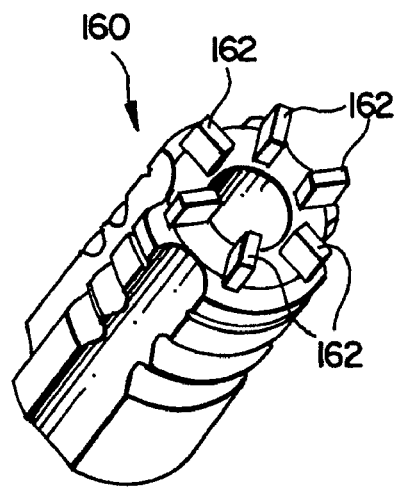

Another alternative embodiment of the invention is shown in FIG. 12. As shown, fixture mount 160 is similarly structured to the embodiment shown in FIG. 9. Rather than including a slotted socket, however, fixture mount 160 includes six extending tabs or splines 162 sized and configured to mate with a socket in a drive tool having six correspondingly sized and oriented slots for receiving the tabs. In this embodiment, when an excessive torque is applied to fixture mount 160, tabs 162 bend or otherwise deform so that the excessive torque cannot be applied and damage to the implant can be prevented.

In addition to providing the desired torque control by means of the interconnections previously described, the torque applied by the drive tool may likewise be limited by employing matingly engaging components that rely on the frictional force between opposing surfaces to transfer the applied torque up until such time as the predetermined maximum torque is reached. When excessive torque is applied, the frictional forces are overcome and the mating surfaces slide against one another, thereby preventing excessive torque from being applied to the implant.

Figure 13:
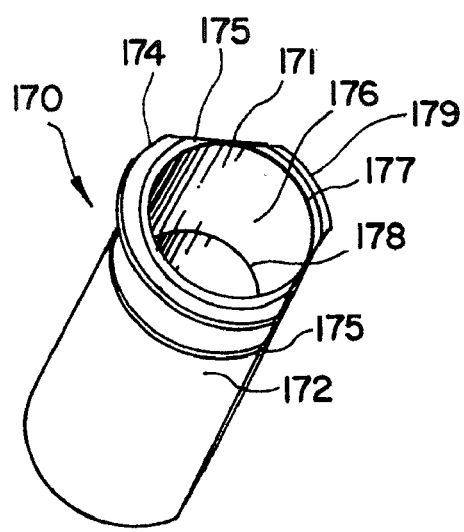

For example, referring to FIG. 13, an alternative embodiment of the present invention is shown and includes a fixture mount 170 having body 172, and a socket 176 on drive tool engaging end 174. Socket 176 has a nonplanar, frustoconical inner surface 171, and is widest at its terminal end 177 and narrowest at its inner end 178. The external surface of body 173 includes a pair of flat surfaces 175 angularly spaced approximately 60 degrees apart so as to provide an orienting lobe 179. Fixture mount 170 is to be employed with a drive tool extension having an outer surface having a corresponding frustoconical shape of substantially the same taper as socket 176. In use, the frustoconical drive end of the drive tool is inserted into socket 176 and a constant axial force is applied to the fixture mount by the drive tool.

The materials for fixture mount 170 and the depth and degree of taper of socket 176 are chosen so that the torque control can be provided by controlling the frictional forces between the drive extension and socket 176. More specifically, the materials and size and shape of the socket are configured and selected such that at a torque less than the predetermined limiting torque, the friction between the opposing surface of socket 175 and the drive tool extension transmit the applied torque and prevent relative motion between the opposing surfaces. However, when the torque applied exceeds the predetermined limit, the rotational force overcomes the frictional forces between the two elements such that the drive tool extension will slip and rotate within socket 176 and transmit no further rotational force such that damaging torque will not be applied.

Figure 14:
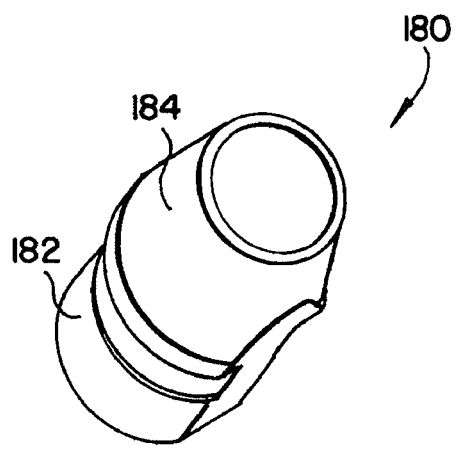

Referring now to FIG. 14, a fixture mount 180 similar to that described with reference to FIG. 13 is shown and includes body 182 and a frustoconical extension 184 of a given taper and length. Fixture mount 180 is intended to be employed with a drive tool having a similarly shaped and sized frustoconical socket. Like the embodiment FIG. 13, before a pre-determined maximum torque is reached, the friction between the drive tool socket and the frustoconical extension 184 of the fixture mount 180 will impart rotational force to the fixture mount and thus to the implant. When an excessive torque is required to further drive the implant, the socket end of the drive tool will begin to slide about the extension 184 to prevent further rotational of fixture mount 180 and the attached implant.

Figure 15:
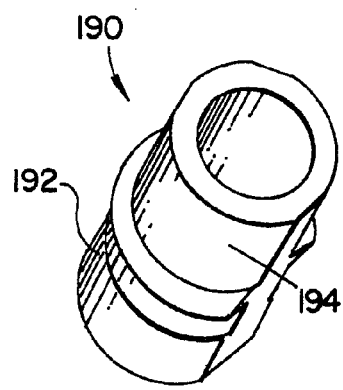

Still a further embodiment of the invention is shown in FIG. 15 wherein a fixture mount 190 includes body 192 and a cylindrical extension 194, rather than one having a frustoconical surface such as previously described with reference to FIG. 14. Fixture mount 190 is to be employed with a drive tool having a cylindrical socket. The outer diameter of extension 194 and the internal diameter of the drive tool socket are closely matched such that a friction fit is created. The friction allows the drive tool to impart a rotational force to the fixture mount 190 until such time as an excessive resistive force is encountered. When a predetermined maximum torque is reached, the drive tool socket slips about extension 194 of the fixture mount 190 and imparts no further rotational force or torque.

Figure 16:
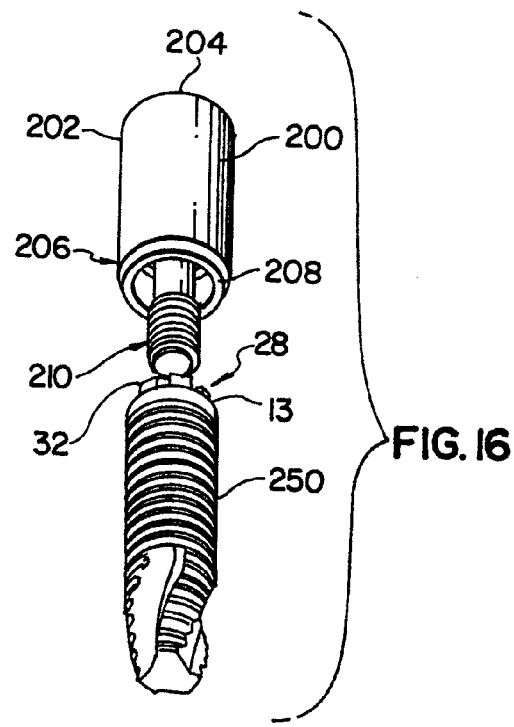
FIG. 16 is a perspective view of an alternative implant drive system of the present invention.

Another embodiment of the present invention is shown in FIG. 16, which, as with the embodiments of FIGS. 13–15 previously described, relies on the frictional forces of opposing but non-interlocking surfaces to apply only limited torque to the fixture mount. As shown in FIG. 16, fixture mount 200 includes a general cylindrical body 202 having a drive tool engaging end 204 and an implant engaging end 206 that terminates in a generally flat annual surface 208. Implant 250 is substantially the same as implant 12 previously described and includes a substantially, flat annular surface 13 at its coronal end between splines 32 and the outermost surface of the implant for engaging annular surface 208 of the fixture mount. As with the embodiment shown in FIG. 1, a retaining screw 210 bears against an internal ledge in fixture mount 200 and is threaded into a central bore of the implant 250 thereby drawing together fixture mount 200 and implant 250. When fixture mount 200 and implant 250 are interconnected, surface 208 of the fixture mount abuts the corresponding surface 13 on the coronal end of the implant. The drive tool engaging end 204 of fixture mount 200 may have any of the mating engagements previously described so as to interface with a drive tool. In this embodiment, the desired torque limiting is achieved by employing the frictional forces between annular surface 208 of the fixture mount and surface 13 on the implant's coronal end, and between the head 17 of the retaining screw and internal shoulder 51 of the fixture mount (FIG. 1). Depending upon the materials selected for the fixture mount and the implant 250, the size of surfaces 208 and 13, and the force applied by the retaining screw 210, the torque applied by the drive tool to the fixture mount 200 is transferred to the implant 250 until such time a predetermined excessive torque is reached, at which time annular surfaces 208 and 13 slip against one another as the frictional forces between them are overcome by the resistive force imparted to the implant.

Figure 17:
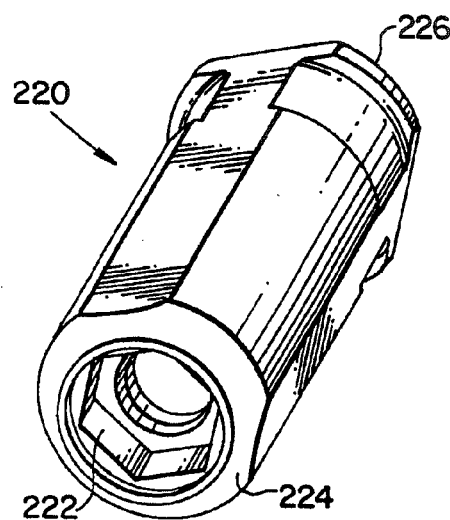
FIG. 17 is a perspective view, similar to FIG. 2, of another alternative fixture mount of the present invention.

As previously explained, the present invention may be used with implants having a variety of designs. For example, a number of conventional implants are constructed so as to have either a polygonal extension or a polygonal socket at the coronal end of the implant. The principles of the present invention can be applied so as to create a drive system and fixture mount for limiting the torque that is applied to such implants. More specifically, referring to FIG. 17, there is shown a fixture mount 220 substantially similar to fixture mount 14 previously described; however, fixture mount 220 does not include splines 64 and spline receptors 70 but instead includes a hexagonal socket 222 at its implant engaging end 224. Socket 222 is sized and configured to matingly receive a correspondingly sized and shaped hexagonal projection on the coronal end of an implant. The drive tool engaging end 226 of fixture mount 220 may be configured like any of the embodiments previously described, or in an equivalent way. Torque limitation is provided by socket 222 such that, when a pre-determined torque is reached socket 222 will deform and spin about the hexagonal extension of the implant so as to prevent further torque from being applied to the implant.

Figure 18:
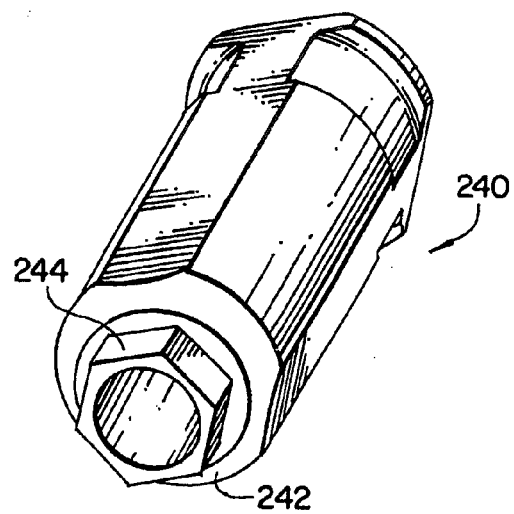
FIG. 18 is a perspective view, similar to FIG. 17, of still another alternative fixture mount of the present invention.

Another alternative for providing torque limitation at the implant engaging end of a fixture mount is shown in FIG. 18. As shown, the fixture mount 240 includes an implant engaging end 242 having a hexagonal extension 244 sized and shaped so as to be received within a corresponding hexagonal recess or socket in the coronal end of an implant. As described with respect to FIG. 17, should a predetermined torque be exceeded, the extension 244 on the implant engaging end 242 of the fixture mount will deform and spin within the socket of the implant 260 so as to prevent damaging torque from being applied to the implant.

For any of the embodiments described herein, the fixture mount may be designed to limit applied torque at either the tool engaging end or the implant engaging end or both. Where the fixture mount employs torque limiting features at each end, either end can be configured to provide the first or primary torque control when a first predetermined torque is applied, with the opposite end operating as a backup mechanism to limit applied torque to a second predetermined torque that is greater than the first predetermined limiting torque should the primary torque limiting structures fail to deform or otherwise operate as intended. Injection molding is the currently-preferred method of manufacturing all of the fixture mounts disclosed herein, and it is believed beneficial to manufacture the entire fixture mount of the same material; however, if desired, the end portions of the fixture mount may be made of a different material than the central portion of the fixture mount body.

Various exemplary structures have been described herein for allowing the fixture mount to releasably engage the adjacent end of a drive tool or implant in an interconnection that provides the desired torque limiting characteristics. In each instance, the interconnection employs an extending portion from one part that is received within a recess in the other. It should be understood that the extensions and recesses can be one or many, and that they may be constructed in a myriad of sizes, shapes and configurations. Accordingly, as used herein, the term "mating element" shall broadly mean any type of extending element or array of extensions for matingly engaging a recess or socket in an adjacent and aligned part, or any type of recess or socket that matingly receives an extending element or elements from an adjacent and aligned part, where the pair of elements releasably mate to form a torque-transmitting joint. The term "corresponding mating element" means and refers to a mating element on one part that is sized and configured to mate with its counterpart element from an opposing part and form a torque-transmitting joint. A hexagonal shaped recess, for example, is a corresponding mating element to an extension having a similarly sized and shaped hexagonal extension. Similarly, an array of extending splines is a corresponding mating element to a socket having an array of recesses that are sized and spaced so as to matingly receive the splines.

As previously explained, providing a means for limiting the torque that is applied to an implant during installation is achieved by appropriately configuring the aligned components and through the selection of materials for those components. Although plastic is the preferred material for the fixture mounts specifically described, the fixture mount may be made of metal as well. For example, the fixture mounts shown in FIGS. 2–12 could be made of titanium and provide the desirable torque limitation provided the walls of the socket (or the diameter of projecting members) were made relatively thin. So configured, the walls of the socket or the projections would permanently deform upon application of a predetermined torque, at which point the drive tool would rotate without transmitting further torque. The metal fixture mount, however, would not have the advantage of being easily modified chair-side for use as a temporary abutment for supporting a temporary prosthesis. Further, permanent deformation of a metal fixture mount might make it impossible to use the fixture mount to remove a partially-installed implant.

While preferred embodiments of this invention have been shown and described, modifications thereof can be made by one skilled in the art without departing from the spirit or teaching of this invention. The embodiments described herein are exemplary only and are not limiting. Many variations and modifications of the system, apparatus and methods are possible and are within the scope of the inventions claimed below. Accordingly, the scope of protection is not limited to the embodiments described herein, but is only limited by the claims which follow, the scope of which shall include all equivalents of the subject matter of the claims.

What is claimed is:

1. A fixture mount for disposition between the adjacent end of a rotatable member and the adjacent end of an aligned implant and for transmitting there between torque of a magnitude less than a damaging torque that would cause damage to the implant, said fixture mount comprising:

an elongate body having a first end portion for engaging the adjacent end of the rotatable member and a second end portion for engaging the adjacent end of the implant;

a first mating element on said body for releasably engaging one of the adjacent ends, said first mating element adapted to engage said one end and transmit torque applied by the rotatable member when the applied torque is less than a first predetermined value, and adapted to disengage from said one end and cease to transmit torque when the applied torque exceeds said first predetermined value, said first predetermined value being less than the implant-damaging torque; and a second mating element on said body for releasably engaging the other one of said adjacent ends, said second mating element adapted to engage said other adjacent end and transmit torque applied by the rotatable member when the applied torque is less than a second predetermined value, and adapted to disengage from said other adjacent end and cease to transmit torque when the applied torque exceeds said second predetermined value, said second predetermined value being higher than said first predetermined value and less than the implant-damaging torque;

wherein said first mating element comprises a socket having an array of recesses, and wherein said socket deforms to the extent that it disengages from said one end and ceases to transmit torque when said first predetermined value is applied.

2. The fixture mount of claim 1 wherein said first mating element is on said first end portion of said body and releasably engages the adjacent end of the rotatable member and said second mating element is on said second end portion of said body and releasably engages the adjacent end of the implant.

3. The fixture mount of claim 1 wherein said second predetermined value is at least 30% higher than said first predetermined value.

4. The fixture mount of claim 1 wherein said first mating element comprises an extending portion, and where said extending portion deforms to the extent that it disengages from said one end and ceases to transmit torque when said first predetermined value is applied.

5. The fixture mount of claim 1 wherein said socket comprises a recess having a polygonal shape in cross section when torque less than said first predetermined value is applied.

6. The fixture mount of claim 1 wherein said first mating element comprises a socket having a frustoconical shaped inner surface.

7. The fixture mount of claim 1 wherein said first mating element comprises an extending portion having a frustoconical shaped outer surface.

8. The fixture mount of claim 1 wherein said first mating element comprises an array of extending portions that deform when said first predetermined value is applied.

9. The fixture mount of claim 1 wherein the rotatable member includes a segment that is received within said socket, and wherein said recesses of said socket have a depth more than one and a half times as long as the segment of the rotatable member that is received within said socket.

10. The fixture mount of claim 1 wherein said first predetermined value is less than 55% of the damaging torque.

11. A fixture mount for disposition between the adjacent end of a rotatable member and the adjacent end of an aligned implant and for transmitting there between torque of a magnitude less than a damaging torque that would cause damage to the implant, said fixture mount comprising:

an elongate body having a first end portion for engaging the adjacent end of the rotatable member and a second end portion for engaging the adjacent end of the implant;

a first mating element on said body for releasably engaging one of the adjacent ends, said first mating element engaging said one end and transmitting torque applied by the rotatable member when the applied torque is less than a first predetermined value, and disengaging from said one end and ceasing to transmit torque when the applied torque exceeds said first predetermined value, said first predetermined value being less than the implant-damaging torque, wherein said first mating element comprises a socket and wherein said socket deforms to the extent that it disengages from said one end and ceases to transmit torque when said first predetermined value is applied, and wherein said socket comprises an array of recesses.

12. The fixture mount of claim 11 wherein the rotatable member includes a segment that is received within said socket and wherein said recesses of said socket have a depth more than one and a half times as long as the segment of the rotatable member that is received within said socket.

13. A fixture mount for engagement with a rotatable member of a drive tool and the coronal end of an implant for transmitting to the implant torque of a magnitude that is less than a damaging torque tat would cause damage to the implant, said fixture mount comprising:

an elongate body having a first end portion for engaging the rotatable member and a second end portion for engaging the coronal end of the implant;

a first mating element on said first end portion of said body for releasably interconnecting with a first corresponding mating element onto rotatable member;

a second mating element on said second end portion of said body for releasably interconnecting with a second corresponding mating element on the coronal end of the implant;

at least one of said end portions of said body being made from a material having an elongation percentage of at least 50 and being configured to deform to the extent that it disengages from its corresponding mating element and ceases to transmit torque when a torque applied to said body by the rotatable member exceeds a first predetermined torque, wherein said first end portion is made of a material having an elongation percentage greater than 60 and a modulus of elasticity less than 10 Gpa, wherein said mating element on said first end portion of said body comprises a socket for receiving and matingly engaging with at least one extension of the corresponding mating element on the rotatable member, and wherein said socket comprises an array of recesses.

14. The fixture mount of claim 13 wherein at least one of said recesses in said array is a slotted opening.

15. The fixture mount of claim 13 wherein said first end portion is made of a material having an elongation percentage greater than 60 and a modulus of elasticity less than 10 Gpa. wherein said mating element on said first end portion of said body comprises a socket for receiving and matingly engaging with at least one extension of the corresponding mating element on the rotatable member, wherein said socket comprises an array of recesses, and wherein said recesses of said may have a depth of at least one and one half times the length of the extensions of the corresponding mating element on the rotatable member.

16. A dental component for disposition between the adjacent end of a rotatable member and the adjacent end of a dental implant said dental component comprising an elongate body having a first portion having a first configuration for engaging the rotatable member and having a second portion for engaging the dental implant wherein said first portion is adapted to deform from said first configuration to a second configuration upon an application of a first predetermined torque to said elongate body by said rotatable member and said first portion is adapted to allow said rotatable member to rotate relative to said first portion upon an application of the first predetermined torque to said elongate body by said rotatable member, and wherein upon removal of said predetermined torque from said elongate body said first portion is adapted to return to a post-torqued configuration substantially similar to said first configuration; and wherein said first portion is made of a material having elongation percentage of at least 50 and a modulus of elasticity less than 45 Gpa.

17. The dental component of claim 16 wherein said first portion comprises a recess with a polygonal cross section.

18. The dental component of claim 16 wherein said first pardon is made of a thermoplastic material.

19. The dental component of claim 16, wherein said first portion in said post-torqued configuration is adapted to engage the rotatable member and rotate said elongate body upon application of a torque less than said predetermined torque.

20. The dental component of claim 16 wherein said second portion disengages from the dental implant upon application of a second predetermined torque, wherein said second predetermined torque is greater than said first predetermined torque.

21. An assembly of dental components comprising:
an implant comprised of a biocompatible metal and having a coronal end; and a fixture mount for engagement with a rotatable member of a drive tool and said coronal end of the implant for transmitting to the implant torque of a magnitude that is less than a damaging torque that would cause damage to the implant, said fixture mount comprising;

an elongate body having a first end portion for engaging the rotatable member and a second end portion for engaging said coronal end of the implant;

a first mating element on said first end portion of said body for releasably interconnecting with a first corresponding mating element on the rotatable member; and a second mating element on said second end portion of said body for releasably interconnecting with a second corresponding mating element on said coronal end of the implant, at least one of said end portions of said body being made from a material having an elongation percentage of at least 50 and being configured to deform to the extent that it disengages from its corresponding mating element and ceases to transmit torque when a torque applied to said body by the rotatable member exceeds a first predetermined torque.

22. The assembly of dental components of claim 21 wherein the first and second end portions are each made from a material having an elongation percentage of at least 50.

23. The assembly of dental components of claim 21 wherein the other of said end portions of said body is configured to transmit to the implant torque applied to said body by the rotatable member when the torque is less than a second predetermined torque that is greater than said first predetermined torque, and to deform to the extent that it disengages from its corresponding mating element and ceases to transmit torque when the torque applied to said body exceeds said second predetermined torque.

* * * * *

UNITED STATES PATENT AND TRADEMARK OFFICE
CERTIFICATE OF CORRECTION

PATENT NO.         : 7,160,109 B2                                              Page 1 of 1
APPLICATION NO. : 10/183211
DATED              : January 9, 2007
INVENTOR(S)        : Christopher Gervais, Jeffery Bassett and Carl Pettersen It is certified that error appears in the above-identified patent and that said Letters Patent is hereby corrected as shown below:

TITLE PAGE: (73)

Please change "Assignee: Sulzer Dental Inc.," to -- Assignee: Zimmer Dental, Inc., --

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,160,109 B2 |
| APPLICATION NO. | : 10/183211 |
| DATED | : January 9, 2007 |
| INVENTOR(S) | : Christopher Gervais, Jeffery Bassett and Carl Pettersen |

Page 1 of 1

It is certified that error appears in the above-identified patent and that said Letters Patent is hereby corrected as shown below:

IN THE CLAIMS:

Claim 11, Column 18, Line 16; Change "socket" (first occurrence) to -- socket, --,;
Claim 12, Column 18, Line 23; Change "socket" (first occurrence) to -- socket, --,;
Claim 13, Column 18, Line 29, Change "tat" to -- that --;
Claim 13, Column 18, Line 37; Change "onto" to -- on the --;
Claim 15, Column 18, Line 62; Change "Gpa." to -- Gpa, --;
Claim 16, Column 19, Line 5; Change "implant" to -- implant, --;
Claim 16, Column 19, Line 8; Change "implant" to -- implant, --;
Claim 16, Column 19, Line 21; Before "elongation" insert -- an --;
Claim 18, Column 19, Line 26; Change "pardon" to -- portion --; and
Claim 21, Column 20, Line 5, Change "comprising;" to -- comprising: --.

Signed and Sealed this

Tenth Day of July, 2007

JON W. DUDAS
*Director of the United States Patent and Trademark Office*